United States Patent [19]
Miller et al.

[11] Patent Number: 5,783,689
[45] Date of Patent: Jul. 21, 1998

[54] ANTIBACTERIAL AND ANTIFUNGAL NUCLEOSIDES

[75] Inventors: Marvin J. Miller, South Bend, Ind.; Julia M. Dolence, Salt Lake City, Utah; Manuka Ghosh, Lawrenceville, N.J.

[73] Assignee: University of Notre Dame, Notre Dame, Ind.

[21] Appl. No.: 745,732

[22] Filed: Nov. 12, 1996

[51] Int. Cl.$^6$ ............................................. C07H 19/067

[52] U.S. Cl. ........................... 536/28.52; 536/28.55; 530/350; 514/19; 514/49; 514/50

[58] Field of Search ........................ 514/19, 49, 50; 530/350; 536/28, 52, 55

[56] References Cited

U.S. PATENT DOCUMENTS

| | | | |
|---|---|---|---|
| 3,575,959 | 4/1971 | Shen et al. | 536/27.23 |
| 4,340,728 | 7/1982 | Endo et al. | 536/28.55 |
| 4,851,519 | 7/1989 | Lambert et al. | 536/28.2 |
| 4,886,785 | 12/1989 | Lambert et al. | 514/50 |
| 4,892,939 | 1/1990 | Sakai et al. | 514/50 |
| 5,010,060 | 4/1991 | Lambert et al | 514/49 |

FOREIGN PATENT DOCUMENTS

| | | |
|---|---|---|
| 0357495 | 3/1990 | European Pat. Off. |
| 0393575 | 10/1990 | European Pat. Off. |
| 57-091994 | 6/1982 | Japan . |
| 57-091995 | 6/1982 | Japan . |
| 57-091996 | 6/1982 | Japan . |
| 57-091997 | 6/1982 | Japan . |
| 57-091998 | 6/1982 | Japan . |
| 57-142998 | 9/1982 | Japan . |
| 61-134397 | 6/1986 | Japan . |
| 64-061494 | 3/1989 | Japan . |
| 7-316108 | 12/1995 | Japan . |
| 8-231584 | 9/1996 | Japan . |
| 2066812 | 7/1981 | United Kingdom . |

OTHER PUBLICATIONS

Yamazaki et al., "Difference Between Cancer Cells and the Corresponding Normal Tissue in View of Stereoselective Hydrolysis of Synthetic Esters," *Biochem. Biophys. Acta*, 1243(3), 300–308 (Apr. 13, 1995).

Mori et al., "Novel Derivatives of 5–Fluorouridine and 5–Fluorouracil Having Potent Antitumor and Lowe Immunosuppressive Activities," *Japanese J. Pharmacology*, 58(3), 269–282 (Mar. 1992).

Ghosh et al., "Design, Synthesis, and Biological Evaluation of Isocyanurate–Based Antifungal and Macrolide Antibiotic Conjungates: Iron Transport–Mediated Drug Delivery," *Bioorg. Med. Chem.*, 3(11), 1519–1525 (1995); *Chem. Abstr.*, 124(3), p. 522, Abstr. No. 25440k (Jan. 15, 1996); only Abstract supplied.

Hu and Miller, J. Org.Chem. 1994, 59, 4858–4861.

M. Ghosh and M. J.Miller, Bioorganic & Medicinal Chemistry, vol. 3, No. 11, pp. 1519–1525, 1995.

Dissertation by Julia A. McKee with Title (partial) "Iron Transport Mediated Drug Delivery", etc. pp. 128–163 and 240–253, presented Aug. '91 and deposited in Univ. of ND Library ca. 1992 (Notre Dame= ND).

*Primary Examiner*—John Kight
*Assistant Examiner*—L. Eric Crane
*Attorney, Agent, or Firm*—William B. Scanlon

[57] ABSTRACT

5'-O-Acyl-5-fluorouridines and 5'-O-acyl-5-sluorocytidines are prepared by the direct acylation of the 5'-hydroxyl group with amino acids under Mitsunobu conditions and the amino acyl derivatives are coupled with other amino acids or peptides to provide antibacterial and antifungal derivatives of the nucleosides. For example, 5-fluorouridine is acylated at the 5'-hydroxyl group with an amino protected L-valine and the acylation product is deprotected to provide 5'-O-(L-valinyl)-5-fluorouridine having activity against Gram-positive bacteria including resistant staphylococcus. Preferred peptide derivatives comprise the tripeptides of ornithine and lysine wherein the terminal amino group is substituted by both hydroxy and acetyl. The latter peptides inhibit the growth of *C. albicans*.

6 Claims, No Drawings

ANTIBACTERIAL AND ANTIFUNGAL NUCLEOSIDES

The United States Government has rights in this invention by virtue of National Institutes of Health Grants Nos. GM25845 and A130988.

BACKGROUND OF THE INVENTION

This invention relates to antimicrobial and antifungal agents. In particular it relates to amino acid and peptide derivatives of the nucleosides, 5-fluorouridine and 5-fluorocytidine having antimicrobial and antifungal properties.

The increasing occurrence of bacteria resistant to the commonly used antibiotics and antibacterial agents has stimulated research efforts to discover new types of antibiotics to which the resistant bacteria are susceptible. Also, the search for compounds that inhibit the growth of opportunistic organisms which cause severe infections in compromised patients continues to increase. Frequently, patients compromised by virus such as the AIDS virus fall prey to fungi which patients with uncompromised immune systems are able to fight off. These infections usually turn out to be fatal in compromised patients.

SUMMARY

5-Fluorouridine (5-FU) and 5-fluorocytidine (5-FC) are acylated on the 5'-position hydroxy group with amino acids and peptides to provide acylation products with antibacterial and antifungal activity. For example, 5'-O-(valinyl)-5-fluorouridine is obtained by the direct acylation of the 5'-hydroxy group of 5-FU under Mitsunobu conditions without accompanying acylation at the ribose hydroxy groups. The valine acylation product inhibits the growth of methicillin-resistant staphylococcus.

Peptide derivatives of 5-FU and 5-FC are prepared by the coupling of the amino acid acyl derivatives, e.g. the valinyl, glycyl, or phenylalanyl, with a di- to octapeptide. In particular the siderophoric ornithine and lysine tripeptides, ($N^5$-acetyl-$N^5$-hydroxy-L-ornithyl)-($N^5$-acetyl-$N^5$-hydroxy-L-ornithyl)-$N^5$-acetyl-$N^5$-hydroxy-L-ornithine and the correspondingly amino substituted lysine tripeptide are incorporated in the peptide chain to provide preferred antifungal compounds.

It appears likely that the amino acid and peptide derivatives transport the nucleosides through the cell membrane via an active transport mechanism or provide binding to the cell wall.

DETAILED DESCRIPTION

The nucleoside derivatives provided by this invention are represented by the following formula 1.

natural amino acid wherein any carboxy, amino, mercapto or hydroxy groups may be substituted; such that when m is an integer of from 2 to 8 each $R^1$ is selected from the same or different members of said group; with the limitations that when m is 0, $R^2$ is other than hydrogen, phenyl or substituted phenyl and, when m is 3 one or $R^1$ is other than 4-(N-acetyl-N-hydroxyamino)butyl or 3-(N-acetyl-N-hydroxyamino)propyl.

The terms used in the foregoing definition of the compounds of the invention have the following meanings herein. "Residue of a natural amino acid", means the group attached to the carbon atom bearing the amino group and the carboxy group of an amino acid found in the naturally occurring proteins and peptides and which is represented by the term Z in the formula $H_2N-CH(Z)-COOH$. Examples of such amino acids that can be used to prepare the compounds of the invention and the accepted 3-letter abbreviations therefore include glycine (Gly), alanine (Ala), valine (Val), isoleucine (Ile), leucine (Leu), serine (Ser), threonine (Thr), proline (Pro), aspartic acid (Asp), glutamic acid (Glu), Lysine (Lys), arginine (Arg), asparagine (Asn), glutamine (Glu), cysteine (Cys), methionine (Met), tryptophane (Trp), phenylalanine (Phr), tyrosine (Tyr), histidine (His), ornithine (Orn), norleucine (Nle), and 2-aminobutyric acid (Abu). In addition to the foregoing amino acids, phenylglycine or a substituted phenylglycine can be used to prepare the compounds of the invention.

The term, "substituted phenyl" refers to phenyl substituted by one or two of the same or different groups selected from lower alkyl, lower alkoxy, halogen, hydroxy, trifluoromethyl, carboxy, carboxamido, lower alkoxycarbonyl, or methylenedioxy, wherein the term lower refers to a straight or branched chain aliphatic group such as methyl, ethyl, n-propyl, isopropyl, t-butyl and the like. Examples of such substituted phenyl groups include the substituted phenylglycine acyl derivatives where, in formula 1 $R^2$ is substituted phenyl or a substituted phenylalanine. $R^2$ is benzyl, eg. 4-methylphenylglycine, 3,4-diethylphenylglycine, 3-chlorophenylglycine, 4-methoxyphenylglycine, 2-fluorophenylglycine, 3-methoxycarbonylphenylglycine, 2,4-dihydroxyphenylglycine, 4-hydroxyphenylglycine, 3-chloro-4-hydroxyphenylglycine, 4-aminocarbonylphenylglycine, 4-methoxyphenylalanine, 3-chaloronphenylalanine, 4-fluorophenylalanine, 3-chloro-4-hydroxyphenylalanine, 4-trifluoromethylphenylalanine, and like substituted phenyl compounds.

As described in the foregoing definition of the compounds represented by the formula 1, any carboxy, amino, mercapto or hydroxy groups present on the residue of the amino acid may be substituted. The amino acids having such groups are serine and threonine which bear a hydroxy group and tyrosine bearing a phenolic hydroxy group; cysteine bears a mercapto group; aspartic acid and glutamic acid bear the carboxy group; and lysine, ornithine and arginine bear

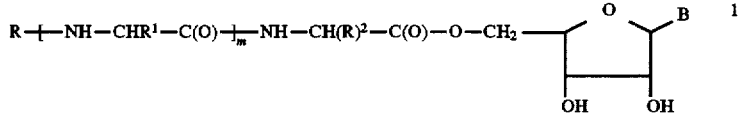

wherein B is 5-fluorouracil-1-yl or 5-fluorocytosine-1-yl;
   m is 0 or an integer of from 1 to 8;
   R is hydrogen or an amino protecting group;
   $R^1$ and $R^2$ are the same or different groups selected from the group of phenyl, substituted phenyl, or the residue of a amino groups. According to the present invention the hydroxy group can be substituted by lower alkyl, for example, methyl or ethyl; with lower alkanoyl, for example acetyl or propionyl; or with an hydroxy protecting group. The mercapto group of cysteine can be substituted by lower alkyl, for example, methyl, ethyl or t-butyl; by lower alkanoyl, for example, acetyl; or by a sulfhydryl protecting group. The carboxy group can be substituted by a carboxy protecting group, or it can be in the carboxylate form such as a salt formed with an alkali metal or alkaline metal salt for example, sodium, potassium or calcium, or an ammonium salt such as the salt formed with ammonia, dimethylamine, diethanolamine, or dicyclohexylamine. The amino group can be mono or disubstituted by lower alkyl, for example, methyl or ethyl; lower alkanoyl, for example, acetyl, chloroacetyl, or propionyl; monosubstituted by hydroxy to form a hydroxylamine group which also can be substituted on the amino group by lower alkanoyl such as acetyl; by an amino protecting group; or the amino group may be in salt form wherein the salt is formed with a mineral acid such as, for example, hydrochloric acid, hydrobromic acid, phosphoric acid, phosphonic acid, or sulfuric acid; a sulfonic acid such as, for example, benzenesulfonic acid, p-toluenesulfonic acid, or methanesulfonic acid; or a carboxylic acid such as, for example, oxalic acid, tartaric acid, maleic acid, benzoic acid, 4-nitrobenzoic acid, and like acids.

As used herein above the terms hydroxy protecting group, amino protecting group, sulfhydryl protecting group and carboxy protecting group, refer to those groups commonly used in the amino acid and peptide art for the temporary protection of the respective functional groups while reactions are carried out at other sites in the molecule. For example, in the peptide coupling reaction a free carboxy group other than the one involved in the desired coupling is protected or blocked to prevent its interference in the desired coupling. Following the coupling to form the desired peptide the carboxy protecting group is removed. While a large number of protecting groups are known and can be used in the preparation of the compounds of the invention, (Protective Groups in Organic Chemistry, J. F. W. McOmie, Ed., Plenum Press, New York. N.Y., 1973 and Protective Groups in Organic Chemistry, T. W. Greene and P. G. M. Wuts, J. W. Wiley and Sons, Inc. NY, 1991), representative examples of amino protecting groups are t-butyloxycarbonyl (t-BOC), benzyloxycarbonyl, p-nitrobenzyloxycarbonyl, trityl, cyclopentyloxycarbonyl, and dimethylethinyloxycarbonyl. Examples of hydroxy protecting groups include benzyl, diphenylmethyl, chloroacetyl, trityl, and allyl. Examples of carboxy protecting groups include the esters, t-butyl, benzyl, diphenylmethyl, p-nitrobenzyl, a silyl ester such as t-butyidimethylsilyl or trimethylsilyl, and the esters formed with N-hydroxysuccinimide and N-hydroxyphthalimide. Examples of sulfhydryl protecting groups include acetyl, chloroacetyl, disulfides formed with mercaptans eg. butylmercaptan or with thiophenols such as thiophenol, wherein deprotection of the sulfydryl group is carried out by reduction of the disulfide.

The compounds of the invention represented by the formula 1 wherein m is 0 are prepared by the direct acylation of the 5'- hydroxyl group of the nucleoside. According to the method, the direct preparation of 5'-amino acid acyl derivatives of 5- fluorouridine and 5-fluorocytidine is carried out under Mitsunobu conditions without requiring protection of the 3- and 4-hydroxy groups of the ribose moiety. According to the process the nucleoside is reacted under an inert atmosphere in an anhydrous inert organic solvent or a mixture of inert organic solvents at a temperature between about 0° C. and about 45° C. with an amino protected amino acid represented by the formula, $RNH-CH(R^2)-COOH$, triphenylphosphine and an azodicarboxylate lower alkyl diester. The reaction mixture is agitated by stirring or shaking. The reagents, triphenylphosphine and the azodicarboxylate, are used in amounts equimolar with the amount of amino acid or, they can be used in slight excess of equimolar.

Azodicarboxylate diesters that can be used in the process include diethyl azodicarboxylate, and diisopropyl azodicarboxylate. Inert organic solvents that can be used include the common solvents such as tetrahydrofuran, dioxane, di-n-butyl ether, dimethylformamide, and dimethylacetamide. Mixtures of organic solvents may also be used.

The amino acid used in the process is represented by the above formula wherein R is an amino protecting group and $R^2$ has the same meanings as defined in formula 1. The reaction product is recovered from the reaction mixture by evaporation of any volatile solvent and reagents and the residue is chromatographed over a suitable material such as silica gel or alumina to provide the 5'-acylated nucleoside.

The process provides selective acylation of the 5'-hydroxy group of 5-FU and 5-FC without any significant acylation of the ribose 3- or 4-hydroxy groups. Following the process and the recovery of the product the amino protecting group R is removed to provide the free amino acid acyl derivative. The latter then can be used to prepare the peptide derivatives represented by the formula 1 wherein m is an integer of from 1 to 8.

In an embodiment of the process, 5-FU is dissolved in a mixture of THF and DMF and with stirring under nitrogen N-(benzyloxycarbonyl)-L-valine is added to the solution followed by the addition of triphenylphosphine and diisopropyl azodicarboxylate. The reaction is carried out at about 25° C. and the product recovered after about 12 hours. The amino protecting group is removed by hydrogenation over a supported palladium catalyst to afford the amino acid acyl derivative, 5'-valinyl-5 -fluorouridine.

In a further embodiment of the process N-(benzyloxycarbonyl)- L-isoleucine is reacted with 5-FC to provide, after removal of the amino protecting group, 5'-isoleucinyl-5-fluorocytidine.

The peptides represented by the formula 1 wherein m is an integer from 1 to 8 can be prepared by standard methods employed in the peptide art for coupling amino acids or for coupling peptides with amino acids or with other peptides. For example, the valinyl 5-FU product obtained in the process is coupled with glycine, alanine, phenylalanine or other amino acid in the form of an active ester of the carboxy group to provide the peptide represented by the formula 1 wherein m is 1 and $R^1$ is hydrogen, methyl, benzyl or the residue of another amino acid. The amino group of the amino acid to be coupled is protected during the coupling reaction and is removed after coupling to provide the free amino group of the dipeptide for further coupling. Various active derivatives of the carboxy group of amino acids or peptide fragments are known and used in coupling reactions. For example, active esters, anhydrides, acid azides or acid halides can serve as active derivatives in the coupling reaction. The peptides also may be prepared by polymer synthesis wherein the amino group of an amino acid may be bonded to a resin via a linking group and the amino acid to be coupled is passed through the resin in an active form for acylation. Further higher peptides can be had by repetition of the process.

Examples of compounds represented by the formula 1 wherein m is 0 are shown in the following Table 1 .

TABLE 1

| R | R² | B |
|---|---|---|
| H | CH₃ | 5-FU[1] |
| H | CH₃ | 5-FC[2] |
| H | —CH(CH₃)₂ | 5-FU |
| H | —CH(CH₃)CH₂CH₃ | 5-FU |
| H | —CH₂CH(CH₃)₂ | 5-FC |
| H | —CH₂OH | 5-FU |
| Boc[3] | —CH(CH₃)₂ | 5-FU |
| H | —(CH₂)₄NH₂ | 5-FU |
| Cbz[4] | —(CH₂)₄NH₂ | 5-FC |
| H | —CH₂CH₂—SCH₃ | 5-FU |
| Boc | —(CH₂)₃NH₂ | 5-FC |
| Boc | —(CH₂)₃NH₂ | 5-FU |
| H | HO—CH(CH₃)— | 5-FC |
| Cbz | HO—CH(CH₃)— | 5-FU |
| H | —CH₂COOH | 5-FU |
| H | —CH₂CH₂COOH | 5-FC |
| H | —CH₂C₆H₅ | 5-FU |
| Boc | —CH₂C₆H₄OH | 5-FU |
| H | —CH₂C₆H₄OH | 5-FC |
| H | —CH₂—C(O)—NH₂ | 5-FC |
| H | —CH₂—C(O)—NH₂ | 5-FU |
| Cbz | —CH₂CH₂C(O)NH₂ | 5-FU |
| H | —CH₂CH₂C(O)NH₂ | 5-FC |

[1] 5-FU = 5-fluorouracil
[2] 5-FC = 5-fluorocytosine
[3] Boc = t-butyloxycarbonyl
[4] Cbz = benzyloxycarbonyl Examples of compounds of the invention represented by the formula 1 wherein m is an integer from 1 to 8, and R=H are shown in the following Table 2.

TABLE 2

| R⫲NH—CHR¹—C(O)⫲ₘ | R² | B |
|---|---|---|
| *Dipeptides (m = 1)* | | |
| Phe— | —CH(CH₃)₂ | 5-FU |
| Phe— | —CH(CH₃)₂ | 5-FC |
| Tyr— | —CH₃ | 5-FU |
| Ile— | H | 5-FU |
| Ser— | —CH(CH₃)₂ | 5-FU |
| Thr— | —CH(CH₃)₂ | 5-FC |
| Thr— | —CH(CH₃)CH₂CH₃ | 5-FU |
| Gln— | —CH₂CH₂—S—CH₃ | 5-FU |
| Asp— | —CH₂C₆H₅ | 5-FC |
| Asn— | —CH₂CH₂COOH | 5-FU |
| Lys— | C₆H₅— | 5-FU |
| *Tripeptides (m = 2)* | | |
| Phe—Ser— | H | 5-FU |
| Phe—Ser— | C₆H₅ | 5-FU |
| Met—Thr— | —CH(CH₃)₂ | 5-FU |
| Ser—Gly— | —CH₃ | 5-FU |
| Ala—Val— | —CH₂CH₃CH₃ | 5-FC |
| Lys—Gly— | —CH₂CH₂—C(O)NH₂ | 5-FC |
| Gln—Asn— | H | 5-FU |
| Ile—Leu— | —CH₃ | 5-FU |
| Trp—Ser— | —CH₂COOH | 5-FU |
| Met—Ser— | —CH(CH₃)₂ | 5-FU |
| Val—Gly— | —C₆H₅ | 5-FU |
| *Tetrapeptides (m = 3)* | | |
| Met—Thr—Gly— | —C₆H₅ | 5-FU |
| Tyr—Gly—Gly— | —CH(CH₃)₂ | 5-FU |
| Lys—Lys—Lys— | —CH(CH₃)₂ | 5-FU |
| Lys—Lys—Lys— | —CH(CH₃)₂ | 5-FC |
| Lys—Lys—Lys— | H | 5-FC |
| Lys—Lys—Lys— | —C₆H₅ | 5-FU |
| ε-N-Hydroxy-ε-N-acetyl Lys— ε-N-hydroxy-ε-N-acetyl Lys— | | |
| ε-N-hydroxy-ε-N-acetyl Lys— ε-N-Hydroxy-ε-N-acetyl Lys— | —CH₂CH₃ | 5-FU |
| ε-N-hydroxy-ε-N-acetyl Lys— ε-N-hydrcxy-ε-N-acetyl Lys— | —CH₂CH₂CH₃ | 5-FU |
| ε-N-Hydroxy-ε-N-acetyl Lys— ε-N-hydroxy-ε-N-acetyl Lys— | —CH(CH₃)₂ | 5-FU |
| ε-N-Hydroxy-ε-N-acetyl Lys— ε-N-hydroxy-ε-N-acetyl Lys— | CH₃ | 5-FC |
| ε-N-Hydroxy-ε-N-acetyl Lys— ε-N-hydroxy-ε-N-acetyl Lys— | —CH(CH₃)CH₂CH₃ | 5-FU |
| Ile—Asp—Val— | CH₃ | 5-FU |
| Trp—Ser—Gly— | —CH₂COOH | 5-FC |
| Val—Gly—Lys— | H | 5-FU |
| ε-N-Hydroxy-ε-N-acetyl Orn— ε-N-hydroxy-ε-N-acetyl Orn— ε-N-hydroxy-ε-N-acetyl Orn— ε-N-Hydroxy-ε-N-acetyl Orn— | —CH₃ | 5-FU |
| ε-N-hydroxy-ε-N-acetyl Orn— ε-N-hydroxy-ε-N-acetyl Orn— | —CH₂—C₆H₅ | 5-FU |
| *Pentapeptides (m = 4)* | | |
| Phe—Gly—Gly—Ile— | —CH(CH₃)₂ | 5-FU |
| Met—Gly—Ser—Val— | —CHCH₂COOH | 5-FU |
| Met—Tyr—Phe—Ala— | —CH₃ | 5-FU |
| Ala—Val—Gly—Val— | —C₆H₅ | 5-FC |
| Lys—Gly—Ile—Leu— | —CH₂CH₂CH₃ | 5-FU |
| Orn—Phe—Phe—Ser— | —CH₂COOH | 5-FU |
| *Hexapeptides (m = 5)* | | |
| Gly—Asp—Phe—Gly—Val | —CH(CH₃)₂ | 5-FU |
| Asn—Lys—Phe—Val—Ile | —CH₃ | 5-FU |
| Asp—Lys—Phe—Val—Ile | —CH₃ | 5-FC |
| Leu—Phe—Val—Gly—Leu | —CH₂CH₂C(O)NH₂ | 5-FU |
| ε-N-Hydroxy-ε-N-acetyl Lys— ε-N-hydroxy-ε-N-acetyl Lys— ε-N-hydroxy-ε-N-acetyl Lys— Val—Gly— | —CH₃ | 5-FU |
| Thr—Gly—Ser—Orn—Leu | —C₆H₅ | 5-FU |
| *Heptapeptides (m = 6)* | | |
| Phe—Ala—Leu—Gly—Gly—Val— | —CH(CH₃)₂ | 5-FU |
| Asn—Phe—Ile—Val—Gly—Ser | C₆H₅ | 5-FC |
| Thr—Gly—Ala—Gly—Leu—Val | —H | 5-FU |
| Met—Ser—Ser—Gly—Trp—Gln | —CH₂C₆H₅ | 5-FU |
| ε-N-Hydroxy-ε-N-acetyl Lys— ε-N-hydroxy-ε-N-acetyl Lys— ε-N-hydroxy-ε-N-acetyl Lys— Gly—Gln—Phe— | —CH₃ | 5-FU 5-FC |
| Asn—Asp—Gly—Phe—Val—Ala | —CH₂CH₂—S—CH₃ | 5-FU |
| *Octapeptides (m = 7)* | | |
| Gly—Phe—Orn—Ala—Ile—Gly—Ser— | CH(CH₃)₂ | 5-FU |
| Gly—Phe—Orn—Ala—Ile—Gly—Ser— | CH(CH₃)₂ | 5-FC |
| Thr—Phe—Ala—Val—Leu—Ser—Ser— | CH₃ | 5-FU |
| Lys—Orn—Ile—Ala—Gly—Gly—Thr— | CH₂COOH | 5-FU |
| Orn—Gly—Gly—Leu—Leu—Val— Asn— | —CH₂CH₂C(O)NH₂ | 5-FU |
| Met—Val—Val—Leu—Asn—Asp— Gly— | —H | 5-FU |
| ε-N-Hydroxy-ε-N-acetyl-Lys— ε-N-hydroxy-ε-N-acetyl-Lys— ε-N-hydroxy-ε-N-acetyl-Lys— Ala—Leu—Val—Gly— | —CH(CH₃)₂ | 5-FU |
| *Nonapeptides (m = 8)* | | |
| Phe—Val—Val—Gly—Leu—Lys—Ser— Gly— | —CH(CH₃)₂ | 5-FU |

TABLE 2-continued

R+NH—CHR¹—C(O)+$_m$

| | R² | B |
|---|---|---|
| Ala—Phe—Val—Gly—Leu—Orn—Ser—Ser | —C₆H₅ | 5-FU |
| Trp—Val—Gly—Val—Leu—Lys—Asn—Ile—ε-N-Hydroxy-ε-N-acetyl Lys—ε-N-hydroxy-ε-N-acetyl Lys—ε-N-hydroxy-ε-N-acetyl Lys—Phe—Ile—Ser—Gly—Val— | —CH(CH₃)CH₂CH₃ | 5-FU |
| | —H | 5-FU |
| Asp—Asp—Gly—Gly—Val—Ala—Phe— | —C₆H₅ | 5-FU |

A preferred group of amino acyl derivatives are represented by the formula 1 wherein m is 0 and R² is methyl, ethyl, isopropyl, n-propyl, but-2-yl, and 2-methylbut-1-yl. An especially preferred amino acyl derivative of the invention is represented by the formula 1 wherein m is 0, R is H and R² is isopropyl, which is obtained by the acylation of 5-FU or 5-FC with valine. The preferred valinyl derivative is obtained by the acylation of 5-FU.

A preferred group of peptide derivatives of the invention are represented by the formula 1 wherein m is an integer of 3 to 8 and the peptide chain incorporates the tripeptide unit represented by the formula 2 below.

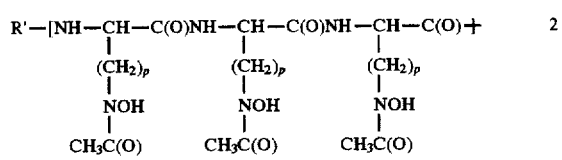

Wherein R' is hydrogen when 2 is the terminal tripeptide or —C(O)— when 2 is not the terminal amino acid residue; and p is the integer 3 or 4.

The tripeptide fragment 2 is obtained with ε-N-hydroxy-ε-N-acetyl-L-lysine p=4, or δ-N-hydroxy-δ-N-acetyl-L-ornithine p=3, as described by Hu, J. and Miller, M. J., J. Org. Chem., 1994, 59, 4858. The preparation of compounds represented by the formula 1 wherein a preferred tripeptide 2 is incorporated is illustrated by the following reaction schemes 1 and 2. In reaction scheme 1, the nucleoside is acylated with glycine and the 5'-glycyl product coupled with the tripeptide 2. In reaction scheme 2, the nucleoside is acylated with phenylglycine and the acylation product coupled with the ornithine or lysine tripeptide 2.

Scheme 1

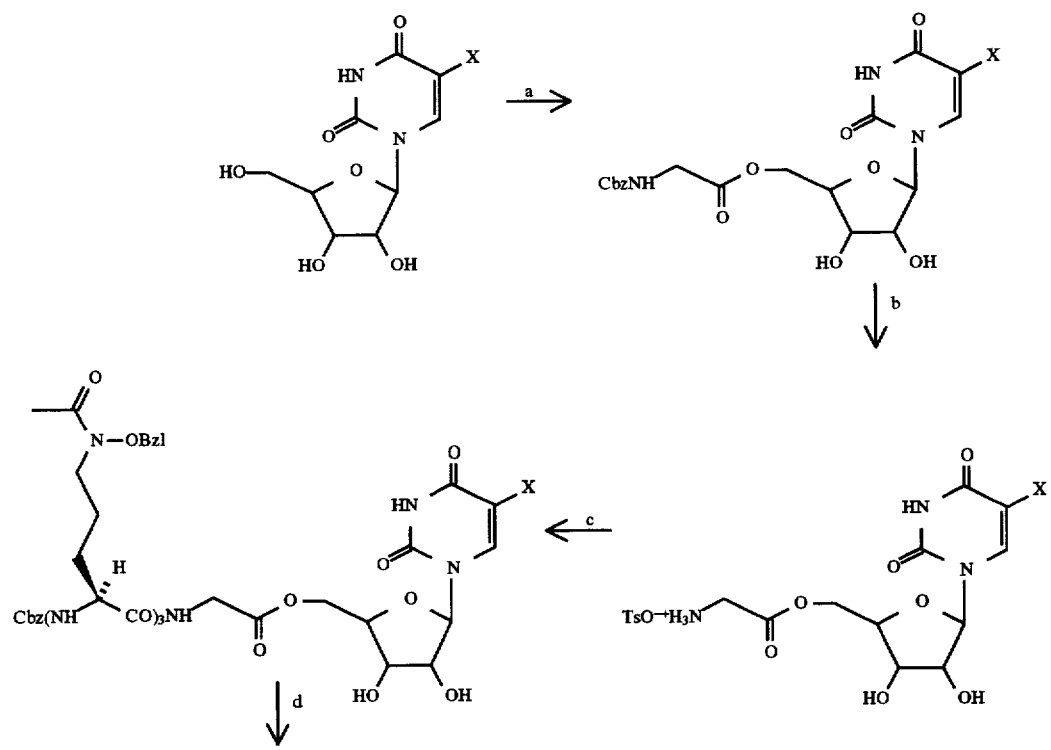

-continued
Scheme 1
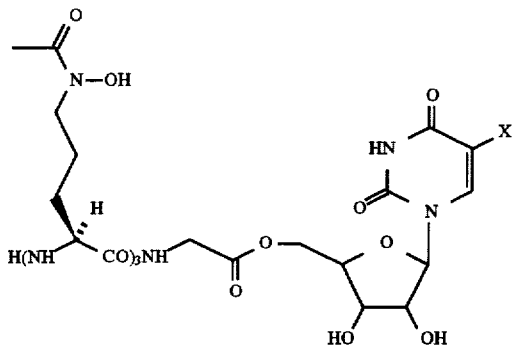
a: Cbzglycine, PPh₃, DIAD, THF, DMF;
b: H₂, Pd—C, TsOH, MeOH;
c: tripeptide ester, NEt₃, DMF, THF;
d: H₂, Pd—C, MeOH, H₂O
Scheme 2
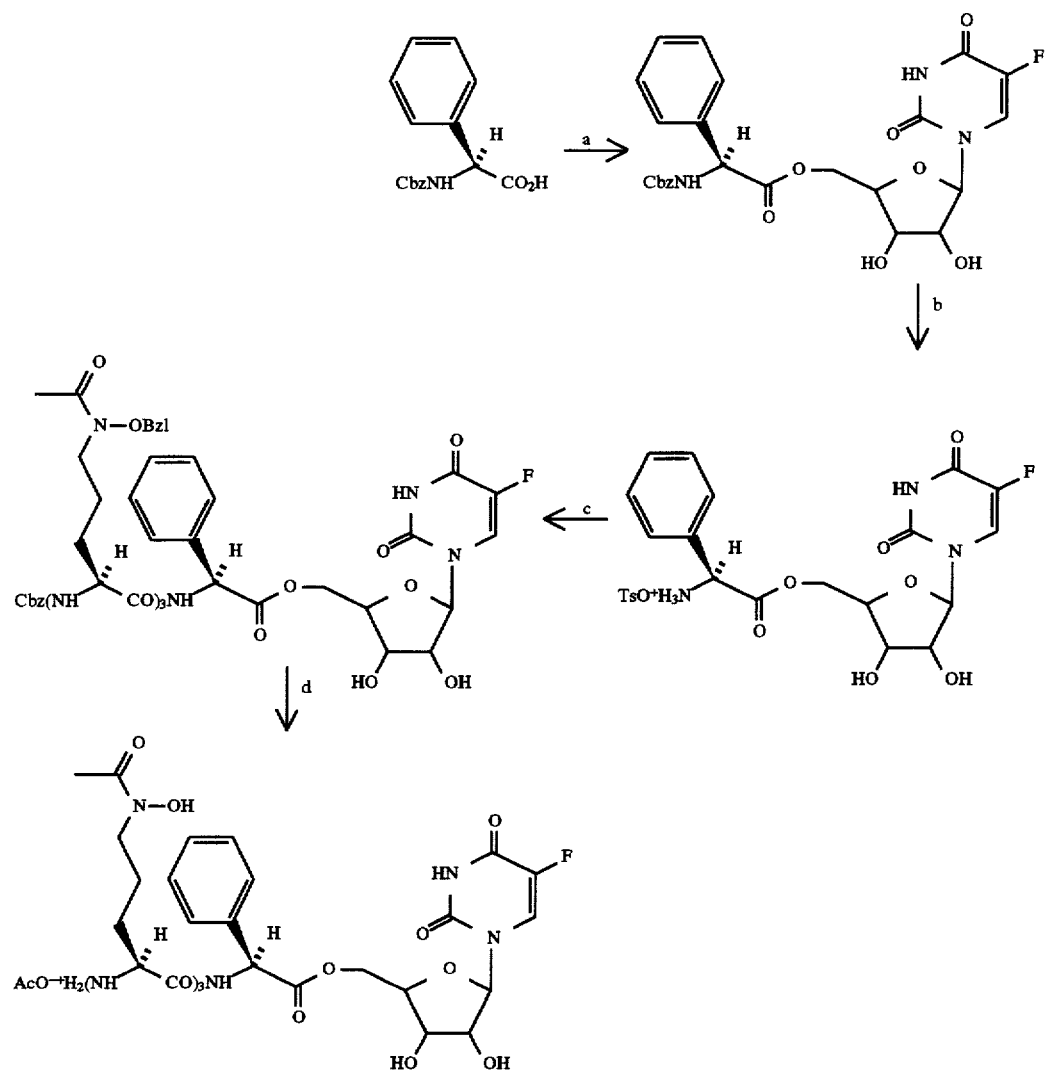

-continued
Scheme 2 a: 5-fluorouridine, PPh$_3$, DIAD, THF, DMF;
b: H$_2$, Pd—C, TsOH, MeOH;
c:, NEt$_3$, DMF, THF;
d: H$_2$, Pd—C, AcOH, MeOH, H$_2$O In the foregoing reaction schemes THF refers to tetrahydrofuran, DMF refers to dimethylformamide, DIAD refers to diisopropyl azodicarboxylate and, AcOH refers to acetic acid.

The tripeptide fragment can be located at any position along the peptide chain represented in the formula 1 except when m is 3 and R$^2$ is hydrogen or phenyl the tripeptide fragment is other than 2.

Preferred compounds wherein the tripeptide 2 is incorporated in the peptide chain are represented when B is 5-fluorouracil and R$^2$ is methyl, ethyl, n-propyl, isopropyl, 2-butyl or 2-methylbutyl.

The tripeptide fragment 2 exhibits siderophoric properties, i.e. it chelates with ionic iron. Virtually all fungi and microbes depend on iron for growth and produce compounds (siderophores) which capture iron for the organism's metabolism. The compounds of the invention wherein a peptide fragment 2 is present in the peptide chain attached to 5-FU or 5-FC exhibit antifungal activity as described herein below. While we do not wish to be bound to any theory or mode of action, it appears likely that the siderophoric peptide fragment 2 enhances the uptake of the compound of the invention into the cell wherein the antifungal property of the compound exerts its effect.

In general it appears that the peptide chains attached to the 5-FU and 5-FC allow the formula I compounds wherein m is 1–8 to be taken up by bacterial and fungal cells via active peptide transport mechanisms. The antifungal nikkomycins and the polyoxins which are natural peptidyl nucleosides are known to be taken up in the cell through active peptide transport.

The compounds of the invention inhibit the growth of microorganisms pathogenic to man and animals. For example the compound 5'-O-(L-valinyl)-5-fluorouridine, represented by the formula 1 wherein m is 0 and R$^2$ is isopropyl, inhibited the in vitro growth of Gram-positive bacteria including the methicillin resistant staphylococci. The compound is also active against Gram-negative microorganisms but to a lesser degree. The following Table 3 lists the minimum inhibitory concentrations obtained by the agar dilution method against Gram-positive and Gram-negative organisms with 5'-O-(valinyl)-5-fluorouridine and comparators ampicillin and 5-FC.

TABLE 3

Minimum Inhibitory Concentrations (µg/mL) vs. Gram-Positive and Gram-Negative Bacteria

| Organism | Ampicillin | 5-FC | Test Compd$^a$ |
| --- | --- | --- | --- |
| *Staphylococcus aureus* X 1.1 | 2 | 8 | 0.5 |
| *Staphylococcus aureus* V 41 | 4 | 8 | 0.25 |
| *Staphylococcus aureus* X 400 | 128 | 8 | 0.25 |
| *Staphylococcus aureus* S13E | 128 | 2 | 0.125 |
| *Staphylococcus epidermis* 70 | 8 | 16 | 0.03 |
| *Staphylococcus epidermis* 222 | 2 | 16 | 1 |
| Streptococcus A C203 | NT$^b$ | NT | NG$^c$ |
| Streptococcus pn PARK | NT | NT | 128 |
| Enterococcus D X66 | 128 | 0.25 | 32 |
| Enterococcus D 2041 | 1 | 4 | 2 |
| E. Coli EC14 | 0.06 | >128 | 128 |

TABLE 3-continued

Minimum Inhibitory Concentrations (µg/mL) vs. Gram-Positive and Gram-Negative Bacteria

| Organism | Ampicillin | 5-FC | Test Compd$^a$ |
| --- | --- | --- | --- |
| E. Coli TEM | 0.03 | " | 16 |
| Klebsiella X26 | 0.008 | " | 32 |
| Enterobacter aerogenes C32 | 0.5 | " | 64 |
| Enterobacter aerogenes EB17 | 0.06 | " | 64 |
| Enterobacter cloacae EB5 | 0.25 | " | 32 |
| Salmonella X514 | 0.06 | " | 32 |
| Salmonella 1335 | 0.125 | " | 32 |
| Serratia X99 | 0.25 | " | 16 |
| Serratia SE3 | 0.5 | " | 16 |
| Shigella sonnei N9 | 0.6 | " | 64 |
| Morganella morganii PR15 | 1 | " | 8 |
| Proteus stu PR33 | 0.06 | " | 32 |
| Proteus rett. C24 | 0.06 | " | 16 |
| Pseudomonas PS19 | 32 | " | 128 |

$^a$Test compound: 5'-O-(valinyl)-5-fluorouridine
$^b$NT = not tested
$^c$NG = no growth The test compound of Table 3,5'-O-(valinyl)-5-fluorouridine, was coupled to the triornithyl peptide represented by the formula 2 wherein p is 3 by following the reaction Scheme 1 above and substituting valine for glycine to provide the tetrapeptide of the invention. The tetrapeptide incorporating the siderophore tripeptide exhibited activity against *Candida albicans* in in vitro tests carried out in Lee's medium at 37° C. Lee, K. L.; Buckley, H. R.; Campbell, C. C., Saubouraudia, 1975, 13, 148. The tetrapeptide gave a 35 mm diameter zone of inhibition at a concentration of the compound of 25 nmol. while at a concentration of 5 nmol. the zone of inhibition was 26 mm.

The compounds of the invention represented by the formula 1 can be used to control bacterial and fungal infections in man and animals when administered in an antibacterially effective or antifungally effective, nontoxic amount. The compounds can be administered parenterally or orally for systemic infections or topically for infections of the skin. The compounds may be formulated in suitable pharmaceutical forms such as solutions, suspensions, ointments, capsules, lozenges, tablets and the like by using standard formulation methods and by employing pharmaceutically acceptable diluents and excipients.

EXAMPLES

The following examples are provided to further describe the invention and are not intended to be limitations thereof.

Example 1
5'-O-(L-Valinyl)-5-fluorouridine tosylate

To a solution of 5-fluorouridine (5-FU, 521 mg, 1.98 mmol) in 6 mL of anhydrous THF-DMF (1:1 under nitrogen was added N-(benzyloxycarbonyl)-L-valine (500 mg, 1.99 mmol), triphenylphosphine (521 mg, 1.98 mmol), and diisopropyl azodicarboxylate (402 mg, 1.98 mmol). The mixture was stirred overnight at 25 °C. The volatile components were removed under reduced pressure and the residue chromatographed over silica gel eluting with methyl alcohol- :chloroform (1:5) to provide 5'-O-[N-(benzyloxycarbonyl)-L-valinyl]-5-fluorouridine (413 mg., 40% yield) as a white solid melting at about 64° C.–67° C.

IR (KBr): 3450 (br), 1700 (br), 1580 cm$^{-1}$.

$^1$HNMR (CDCl$_3$): δ0.91 (d, J=6.6 Hz, 3H), 0.97 (d, J=6.6 Hz, 3H), 2.03–2.23 (m, 1H), 3.85–4.55 (m, 7H), 5.01–5.15 (m, 2H), 5.46 (d, J+8.1 Hz, 1H), 5.79 (d, J=2.7 Hz, 1 H), 7.28–7.38 (m, 5H), 7.64 (d, J=6.0 Hz, 1H), 10.27 (br s, 1H).

$^{13}$C NMR (CDCl$_3$): δ172.11, 157.41 (d, J=104 Hz, for C-4), 156.55, 149.58, 140.51 (d, J=944 Hz, for C-5), 124.39 (d, J=134 Hz, for C-6), 135.91, 128.51, 128.23, 128.08, 89.85, 81.69, 77.20, 74.39, 69.88, 67.22, 63.94, 59.48, 30.81, 18.95, 17.58.

Elemental anal. Calcd. for C$_{22}$H$_{25}$N$_3$O$_9$F·H$_2$O: C, 51.56; H, 5.31; N, 8.2. Found: C, 51.62; H, 5.33; N, 7.92.

To a solution of the compound prepared as described above (85 mg., 0.17 mmol) in 3.0 mL of methyl alcohol (spectral grade) was added p-toluenesulfonic acid (33 mg, 0.17 mmol). The solution was deoxygenated with nitrogen, and then 10% Pd-C (17 mg, 20% w/w) was added. The suspension was stirred under 1 atm of hydrogen for 45 min after which TLC indicated that the reaction was complete. The catalyst was removed by filtration through a short pad of Celite and the solution was concentrated to afford the title compound (98%) as a white solid.

Example 2
5'-O-(L-Alanyl)-5-fluorouridine Tosylate

The title compound is prepared by following the procedures described by Example 1 and by substituting N-(benzyloxycarbonyl)- L-alanine for valine.

Example 3
5'-O-(L-Leucinyl)-5-fluorouridine tosylate

The title compound is prepared by following the procedures of Example 1 and by substituting L-leucine for valine.

Example 4
N-(Benzyloxycarbonyl)-glycyl-5-fluorouridine

5-Fluorouridine (0.300 g, 1.144 mmol, Sigma) was suspended in 4.0 mL of anhydrous tetrahydrofuran under nitrogen. Dry DMF (0.25 mL) was added. Slowly, the solid dissolved. Cbz glycine (0.239 g, 1.142 mmol, Aldrich), triphenylphosphine (0.300 g, 1.144 mmol), and DIAD (0.220 g, 1.088 mmol) were added. The yellow solution was stirred for 48 h. The solution was concentrated under reduced pressure and chromatographed eluting successively with 1:20 MeOH:CHCl$_3$, 1:10 MeOH:CHCl$_3$, then 1:5 MeOH:CHCl$_3$ to provide 0.137 g (27%) of the title compound as a colorless oil. (The same reaction without the DMF as a cosolvent resulted in an isolated yield of only 13%): IR (TF) 3300 (br), 1710, 1670 cm$^{-1}$; $^1$H NMR (300 MHz, methanol-d$_4$) δ3.95 (s, 2H, NHCH$_2$CO), 4.05–4.20 (m, 3H, ribose H-2',3', 4'), 4.35–4.50 (m, 2H, ribose H-5'), 5.09 (s, 2H, benzylic H), 5.81 (m, 1 H, ribose H-1'), 7.25–7.40 (m, 5H, aromatic H), 7.83 (m, 1 H, vinylic H); $^{13}$C NMR (75 MHz, methanol-d$_4$) δ43.41, 64.90, 67.82, 70.65, 74.99, 82.85, 91.43, 125.95 (d, J=34.7 Hz, C 4), 128.77, 128.97, 129.40, 137.86, 141.74 (d, J=234.3 Hz, C5), 150.74, 158.96, 159.24 (d, J=26.2, C4), 171.55; TLC (methanol-chloroform, 1:5) R$_f$=0.35; exact MS (EI) calcd for C$_{19}$H$_{20}$N$_3$O$_9$F: m/z 453.1184. Found: m/z 453.1174.

Example 5
Glycyl 5-Fluorouridine p-Toluenesulfonic Acid Salt

The amino protected glycyl derivative prepared as described by Example 4 (0.066 g, 0.152 mmol) and p-TsOH (0.029 g, 0.152 mmol) was dissolved in 2.0 mL of methanol. 10% Pd-C (0.014 g, 20% w/w) was added and the solution was stirred under a hydrogen atmosphere for 45 min. The solution was filtered through a plug of cotton to remove the catalyst. The filtrate was concentrated to provide 0.078 g of a colorless oil: IR (TF) 3640–2680 (br), 1755, 1705, 1685, 1655 cm$^{-1}$; $^1$H NMR (300 MHz, methanol-d$_4$) δ 2.36 (s, 3H, ArCH$_3$), 3.94 (d, J=6.6 Hz, 2H, NHCH$_2$CO), 4.15–4.25 (m, 3H, ribose H-2', 3', 4'), 4.45–4.58 (m, 2H, ribose H-5'), 5.77 (dd, J=0.9 and 3.6 Hz, 1H, ribose H-1'), 7.23 (d, J=8.1 Hz, 2H, aromatic H), 7.70 (d, J=8.1 Hz, 2H, aromatic H), 7.82 (d, J=6.6 Hz, 1H, vinylic H); $^{13}$C NMR (75 MHz, methanol-d$_4$) δ 21.28, 41.14, 66.04, 70.70, 74.56, 82.51, 92.24, 126.47 (d, J=35.1 Hz, C6), 126.85, 129.79, 140.16, 141.78, 143.11, 143.25, 150.69, 159.14 (d, J=26.5 Hz, C4), 168.29; MS (positive ion FAB, glycerol) m/z 320.4 (M-TsO-).

Example 6
N-(Benzyloxycarbonyl)-phenylalycyl-5-fluorouridine

5-Fluorouridine (0.322 g, 1.23 mmol) was suspended in 2.0 mL of anhydrous tetrahydrofuran and 1.0 mL of anhydrous DMF under nitrogen. Cbz-L-phenylglycine (0.350 g, 1.23 mmol), triphenylphosphine (0.322 g, 1.23 mmol) and DIAD (0.236 g, 1.17 mmol) were added. The yellow solution was stirred for 16 h. The solution was concentrated under reduced pressure and chromatographed eluting successively with 1:10 MeOH:CHCl$_3$, then 1:5 MeOH:CHCl$_3$ to provide 0.265 g (41%) of the title compound as a colorless oil: IR (TF) 3330 (br), 2820, 1755–1650 (br), 1510 cm$^{-1}$; $^1$H NMR (300 MHz, methanol-d$_4$) δ 3.77–3.85 (m, 2H, ribose H-2', 3'), 4.11 (m, 1H, ribose H-4'), 4.36 (dd, J=2.4 and 12.3 Hz, 1H, ribose H- 5'), 4.46 (dd, J=3.9 and 12.3 Hz, 1H, ribose H-5'), 5.09 (m, 2H, benzylic H), 5.34 (s, 1H, NCHCO), 5.76 (m, 1H, ribose H-1'), 7.25 –7.45 (m, 10H, aromatic H), 7.64 (d, J=6.6 Hz, 1H, vinylic H); $^{13}$C NMR (75 MHz, methanol-d$_4$) δ 59.77, 65.15, 67.68, 67.79, 70.49, 74.66, 82.99, 90.72, 125.57 (d, J=34.1 Hz, C6), 128.32, 128.57, 128.64, 128.70, 128.78, 128.86, 129.21, 129.26, 129.59, 129.67, 129.80, 129.86, 136.96, 137.57, 137.62, 141.51), (d, J=233.6 Hz, C5), 150.53, 157.86, 159.00 (d, J=26.2, C4), 171.99; TLC (methanol-chloroform, 1:5) R$_f$=0.52; exact MS (EI) calcd for C$_{25}$H$_{24}$N$_3$O$_9$F: m/z 529.1496. Found: m/z 529.1496.

Example 7
L-Phenylglycyl 5-Fluorouridine p-Toluenesulfonic Acid Salt

The amino protected phenylglycyl derivative prepared as described by Example 6 (0.030 g, 0.057 mmol) and p-TsOH (0.011 g, 0.057 mmol) were dissolved in 2.0 mL of methanol. 10% Pd- C (0.007 g, 20% w/w) was added and the solution was stirred under a hydrogen atmosphere for 30 min. The solution was filtered through a plug of cotton to remove the catalyst. The filtrate was concentrated to provide 0.034 g (100%) of the free amino tosylate salt as a colorless oil: IR (TF) 3520–2820 (br), 1770, 1730, 1680 cm$^{-1}$; $^1$H NMR (300 MHz, methanol-d$_4$) δ 2.36 (s, 3H, ArCH$_3$), 3.80 (m, 2H, ribose H-2',3'), 4.08 (m, 1H, ribose H-4'), 4.44 (dd, J=12.3 and 2.7 Hz, 1H, ribose H-5'), 4.59 (dd, J=12.3 and 4.8 Hz, 1H, ribose H- 5'), 5.26 (s, 1H, NCHCO), 5.67 (m, 1H, ribose H-1'), 7.23 (d, J=8.1 Hz, 2H, aromatic H), 7.46 (m, 5H, aromatic H), 7.54 (d, J=6.6 Hz, vinylic H), 7.70 (d, J=8.1 Hz, 2H, aromatic H); $^{13}$C NMR (75 MHz, methanol-d$_4$) δ 21.29, 57.75, 66.50, 70.71, 74.38, 82.79, 91.91, 126.10 (d, J=34.4 Hz, C6), 126.88, 129.23, 129.72, 130.58, 131.34, 132.77, 141.64 (d, J=234.6 Hz, C5), 141.69, 150.69, 159.02 (d, J=26.2 Hz, C4), 169.32 MS (positive ion FAB, glycerol) m/z 568 (M+1), 396 (M-TsO$^-$).

Example 8

L-Phenylalanyl-5-fluorouridine p-Toluenesulfonic Acid Salt

The title compound is prepared by following the procedures described in Examples 5 and 6 and by substituting L-phenylalanine for L-phenylglycine.

Example 9

($N^5$-Acetyl-$N^5$hydroxy-L-ornithyl)-($N^5$-acetyl-$N^5$-hydroxy-L-ornithyl)-($N^5$-acetyl-$N^5$hydroxy-L-ornithyl)-L-phenylglycine tert-Butoxycarbonyl-L-phenylglycine Benzyl Ester

N-tert-Butoxycarbonyl-L-phenylglycine (2.00 g, 7.48 mmol) and KHCO$_3$ (0.748 g, 7.48 mmol) were dissolved in 10.0 mL of anhydrous DMF under nitrogen. Benzyl bromide (1.28 g, 7.48 mmol) was added dropwise and the solution was stirred overnight then poured into 100 mL of ethyl acetate. The solution was washed with water, brine, dried, filtered and concentrated to provide an oil which was crystallized from ethyl acetate and hexanes to afford 2.33 g (91%) of white crystals: mp 60°–62° C.; IR (KBr) 3380, 1740, 1730, 1690 cm$^{-1}$; $^1$H NMR (300 MHz, CDCl$_3$) δ 1.43 (s, 9H, C(CH$_3$)$_3$), 5.15 (s, 2 H, benzylic H), 5.37 (d, J=7.5 Hz, 1H, NCHCO), 5.57 (m, 1H, NH), 7.15–7.35 (m, 10H, aromatic H); $^{13}$C NMR (75 MHz, CDCl$_3$) δ 28.26, 57.71, 67.21, 80.10, 127.12, 127.84, 128.21, 128.36, 128.43, 128.80, 135.17, 136.79, 154.76, 170.92; exact MS (EI) calcd for C$_{20}$H$_{23}$NO$_4$: m/z 341.1627. Found: m/z 341.1625.

($N^5$-Acetyl-$N^5$-benzyloxy-$N^2$-benzyloxycarbonyl-L-ornithyl)-($N^5$-acetyl-$N^5$-benzyloxy-L-ornithyl)-($N^5$-acetyl-N-benzyloxy-L-ornithyl)-L-phenylglycine Benzyl Ester

The t-Boc protected phenylglycine benzyl ester prepared as described above (0.045 g, 0.132 mmol) was dissolved in 1.0 mL of anhydrous methylene chloride under nitrogen and cooled to 0° C. TFA (0.25 mL) was added and the solution was stirred at 0° C. for 1 h. The solvents were removed by repeated evaporation with benzene and hexanes to give an oil. The oil was dissolved in 2.0 mL of distilled water and tripeptide active ester ($N^5$-acetyl-$N^5$- benzyloxy-$N^2$-benzyloxycarbonyl-L-ornithyl)-($N^5$-acetyl-$N^5$-benzyloxy-L-ornithyl)-($N^5$-acetyl-$N^5$-benzyloxy-L-ornithyl)-L-phenylglycine formed with N-hydroxysuccinimide (0.149 g, 0.128 mmol) in 2.0 mL of ethyl acetate was added, quickly followed by KHCO$_3$ (0.038 g, 0.380 mmol) and the solution was stirred for 14 h. The solution was diluted with ethyl acetate and washed with 5% KHCO$_3$, water, brine, dried, filtered and concentrated to provide a white foam. The foam was purified by radial chromatography eluting with 1:50 MeOH:CHCl$_3$, then 1:20 MeOH:CHCl$_3$ to give 0.136 g of an oil. A slight contaminant was removed by preparative thin layer chromatography to afford 0.096 g (65%) of a yellow oil: IR (TF) 3400, 2960, 1740, 1650 cm$^{-1}$; $^1$H NMR (CDCl$_3$) δ 1.45–1.80 (m, 12H, CH$_2$), 2.04 (s, 3H, CH$_3$CO), 2.05 (s, 3H, CH$_3$CO), 2.08 (s, 3H, CH$_3$CO), 3.40–3.55 (m, 3H, CH$_2$N), 3.85–4.10 (m, 3H, CH$_2$N), 4.30–4.45 (m, 1H, NCHCO), 4.50–4.67 (m, 2H, NCHCO), 4.77 (m, 6H, benzylic H), 5.05 (s, 2 H, benzylic H), 5.07 (s, 2H, benzylic H), 5.54 (d, J=7.5 Hz, 1H, NCHAr), 5.70 (d, J=7.8 Hz, 1H, NH), 7.10–7.15 (m, 3H, aromatic H), 7.20–7.40 (m, 27H, aromatic H), 7.60 (m, 1H, NH); $^{13}$C NMR (75 MHz, CDCl$_3$) δ 20.28, 20.31, 20.36, 23.06, 23.14, 23.20, 29.37, 30.36, 43.85 (m), 51.46, 51.96, 53.42, 56.50, 66.73, 66.96, 76.18, 76.24, 76.30, 127.37, 127.68, 127.85, 127.92, 128.04, 128.27, 128.30, 128.36, 128.61, 128.70, 128.84, 129.09, 134.31, 135.23, 135.87, 136.34, 156.29, 170.29, 171.11, 171.77, 172.13, 172.84, 172.87; TLC (methanol-chloroform, 1:20) R$_f$=0.26; MS (positive ion FAB, glycerol) m/z 1163 (M+1)

The protected tripeptide acylation product prepared as described above (0.094 g, 0.081 mmol) was dissolved in 2.0 mL of MeOH and 2.0 mL of deionized, distilled water. 10% Pd-C was added and the solution was subjected to a hydrogen atmosphere for a total of 6 h. The catalyst was removed by filtration through a plug of cotton and the solution was concentrated under reduced pressure. The residue was redissolved in 1.0 mL of deionized distilled and lyophilized to afford 0.0457 g (87%) of the title compound as a white solid: FeCl$_3$ positive (red-purple); mp 135–137° C.; IR (KBr) 3400 (br), 1630 (br), 1500 cm$^{-1}$; $^1$H NMR (300 MHz, D$_2$O) δ 1.35–1.80 (m, 12H, CH$_2$), 1.93 (m, 9H, CH$_3$CO), 3.35–3.500 (m, 6H, CH$_2$N), 3.85 (t, 1H, NCHCO), 4.15–4.25 (m, 2H, NCHCO), 4.97 (s, 1H, NCHAr), 7.19 (s, 5 H, aromatic H); $^{13}$C NMR (75 MHz, D$_2$O) δ 19.29, 21.33, 22.21, 22.35, 27.93, 28.05, 46.93, 47.14, 47.21, 52.52, 53.39, 59.02, 126.95, 127.98, 128.80, 138.13, 169.24, 171.95, 172.79, 173.75, 173.81, 173.94, 175.32 ; MS (positive ion FAB, m-nitrobenzyl alcohol/glycerol) m/z 668 (m+1).

Example 10

($N^5$-acetyl-$N^5$-hydroxy-L-ornithyl)-($N^5$-acetyl-$N^5$-hydroxy-L-ornithyl)-ac($N^5$acetyl-$N^5$-hydroxy-L-ornithyl)-(L-phenylglycyl)-5-fluorouridine Acetate Salt

L-Phenylglycyl 5-fluorouridine p-toluenesulfonic acid salt prepared as described by Example 7 (0.094 g, 0.177 mmol) was dissolved in 1.0 mL of dry dimethylformamide under nitrogen. The protected ornithyl tripeptide active ester formed with N- hydroxysuccinimide which was used in the preparation described by Example 9 was dissolved in THF and added to the above solution, followed by triethylamine (0.040 g, 0.355 mmol). The solution was stirred for 16 h, then the solution was concentrated under reduced pressure and diluted with 100 mL of ethyl acetate. The solution was repeatedly washed with water, brine, dried, filtered and concentrated to give a white foam. ($N^5$-Acetyl-$N^5$-benzyloxy-$N^2$-benzyloxycarbonyl-L-ornithyl)-($N^5$-acetyl-$N^5$-benzyloxy-L-ornithyl)-($N^5$-acetyl-$N^5$-benzyloxy-L-ornithyl)-(L-phenylglycyl)-5-fluorouridine was isolated in 54% yield (0.125 g) as a clear oil following radial silica gel chromatography eluting with chloroform, 1:50 MeOH:CHCl$_3$, and 1:20 MeOH:CHCl$_3$;IR (TF) 3295, 1740, 1700, 1650 cm$^{-1}$; $^1$H NMR (300 MHz, CDCl$_3$) δ 1.45–1.80 (m, 12H, CH$_2$), 2.02 (s, 3H, CH$_3$CO), 2.05, (s, 3H, CH$_3$CO), 2.06 (s, 3H, CH$_3$CO), 3.40–3.60 (m, 4H, CH$_2$N), 3.75–4.05 (m, 4H, CH$_2$N and ribose H'), 4.10–4.20 (m, 2 H, ribose H'), 4.25–4.50 (m, 4H, NCHCO and ribose H'), 4.55–4.85 (m, 7 H, NCHCO and benzylic H), 5.01 (d, J=12.6 Hz, 1H, benzylic H), 5.07 (d,J=12.6 Hz, 1H, benzylic H), 5.56 (d,J=7.2 Hz, 1H, NCHAr), 5.63 (m, 1H, ribose H-1'), 5.95 (d,J=6.6 Hz, 1H, NH), 7.20–7.45 (m, 27H, aromatic and NH), 7.55 (m, 1H, NH), 7.86 (m, 1H, vinylic H); $^{13}$C NMR (75 MHz, CDCl$_3$) δ 20.22, 20.36, 23.13, 23.35, 28.56, 29.58, 44.34 (m), 52.10, 52.75, 54.53, 57.22, 63.74, 66.91, 69.23, 73.77, 76.29, 76.43, 77.20, 81.64, 91.95, 125.63 (d, J=33.5 Hz, C6), 127.38, 127.83, 128.01, 128.07, 128.42, 128.55, 128.69, 128.80, 128.94,128.98, 129.00, 129.14, 129.16, 134.16, 134.30, 135.56, 136.24, 140.52 (d, J=236.7 Hz, C5), 149.50, 156.57, 156.60, 157.03 (d, J=26.3 Hz, C4), 169.63, 171.26, 172.59, 172.79; TLC (methanol-chloroform, 1:10) R$_f$=0.23; MS (positive ion FAB, m-nitrobenzyl alcohol/glycerol) m/z 1317 (M+1).

The protected tripeptide acylation product obtained as described above (0.100 g, 0.076 mmol) was dissolved in 2.0 mL of methanol and 2.0 mL of deionized distilled water. 10% Pd-C (0.020 g, 20% w/w) was added and the solution was hydrogenated at atmospheric pressure for 3 h. The catalyst was removed by filtration through a plug of cotton and the solution was concentrated. The resulting oil was not water soluble which may indicate incomplete deprotection. The solution was again subjected to the reaction conditions, but again, incomplete deprotection apparently was observed. The residue was dissolved in 1.0 mL of dioxane and 1.0 mL of deionized distilled water. Glacial acetic acid (3.9 mL, 0.0684 mmol), and 13 mg of 10% Pd-C were added. The solution was placed under a hydrogen atmosphere for 2 h. The solution was filtered and concentrated and redissolved in 1.0 mL of deionized distilled water and lyophilized to afford 0.063 g of the title compound as a tan solid: FeCl₃ positive (red-purple); mp 51–53° C.; IR (KBr) 3620–3100 (br), 1750, 1695 cm⁻¹; ¹H NMR (300 MHz, D₂O), δ 1.40–1.70 (m, 12H, CH₂), 1.72 (s, 3H, CH₃CO2), 1.92 (m, 6H, CH₃CON), 1.95 (s, 3H, CH₃CON), 3.30–3.70 (m, 8H, CH₂N and ribose H'), 3.85 (m, 1H, ribose H'), 4.05 (m, 1H, NCHCO), 4.20 (m, 3H, NCHCO and ribose H-5'), 4.40 (m, 1H, NCHCO), 5.33 (s, 1H, ribose H-1'), 5.53 (m, 1H, NCHAr), 7.21 (s, 5H, aromatic H), 7.41 (d, J=6.0 Hz, 1H, vinylic H); ¹³C NMR (75 MHz, D₂O), δ 19.38, 21.44, 22.23, 22.38, 23.13, 28.10, 28.19, 47.04, 47.17, 47.27, 52.62, 53.13, 53.40, 57.35, 62.58, 64.43, 65.64, 69.20, 69.23, 72.11, 73.49, 81.84, 89.42, 90.19, 125.13 (d, 0991 J=34.3, C6), 127.74, 129.32, 129.37, 134.63, 140.59 (d, J=234.3 Hz, C5), 150.07, 159.36 (d, J=24.0 Hz, C4), 169.72, 171.10, 172.84, 173.86, 173.99; MS (positive ion FAB, m-nitrobenzyl alcohol/glycerol) m/z 912 (M+1).

Example 11

(N⁵-hydroxy-L-ornithyl)-(N-⁵-acetyl-N-⁵-hydroxyl-L orinithyl)-(acetyl N-⁵-hydroxyl-L-ornithyl)-(glycyl)-5-flourouridine Glycyl 5-fluorouridine p-TsOH salt prepared as described by Example 5 (0.141 g, 0.287 mmol) was dissolved in 1.0 mL of dry dimethylformamide under nitrogen. Triethylamine (0.058 g, 0.573 mol) was added, quickly followed by the protected ornithyl tripeptide active ester in THF. The solution was stirred for 16 h. The solution was concentrated under reduced pressure and diluted with 100 mL of ethyl acetate. The organic phase was repeatedly washed with water, brine, dried, filtered and concentrated to give a white foam. The tripeptide acylation product was isolated in 39% yield (0.143 g) as a white foam following radial silica gel chromatgraphy, eluting with chloroform, 1:50 MeOH:CHCl₃, and then 1:20 MeOH:CHCl₃: mp 65°–67° C.; IR (TF) 3300, 2930, 1750, 1720, 1710, 1655 cm⁻¹; ¹H NMR (300 MHz, methanol-d4) δ 1.55–1.85 (m, 12H, CH₂), 2.01 (s, 9H, CH₃CO), 3.45–3.80 (m, 6H, NHCH₂CO, NHCHCH₂, and ribose H), 3.96 (q, 2H, ribose H), 4.05–4.25 (m, 4H, CH₂N, ribose H), 4.30–4.50 (m, 4H, CH₂N), 4.82 (s, 6H, benzylic H), 5.02 (q, 2H, benzylic H), 5.81 (d, J=3.3 Hz, 1H, ribose H-1'), 7.25–7.40 (m, 20H, aromatic H), 7.80 (d, J=6.6 Hz, 1H, vinylic H); ¹³C NMR (75 MHz, methanol-d4) δ 20.55, 24.22, 29.90, 30.03, 31.19, 41.94, 45.30, 45.36, 53.81, 54.11, 55.81, 64.86, 67.62, 70.60, 74.78, 77.01, 79.22, 82.63, 91.48, 126.00 (d, J=34.7 Hz, C6), 128.62, 128.87, 129.34, 129.56, 129.71, 129.76, 129.78, 129.85, 130.44, 130.49, 135.69, 137.76, 141.63 (d, J=233.7 Hz, C5), 150.65, 158.23, 159.08 (d, 1045 J=26.0 Hz, C4), 170.47, 173.61, 173.96, 174.14, 174.17, 174.57; TLC (methanol-chloroform, 1:10) R_f=0.32; MS (positive ion FAB glycerol) m/z 1241 (M+1), 1263 (M+Na⁺), 1279 (M+K⁺). The tri-O-benzylated acylation product (0.121 g, 0.0976 mmol) was dissolved in 2.0 mL of methanol and 1.0 mL of deionized distilled water. 10% Pd-C (0.024 g, 20% w/w) was added and the solution was hydrogenated at atmospheric pressure for 3 h. The catalyst was removed by filtration and the solution was concentrated. The resulting oil was dissolved in 1.0 mL of deionized distilled water and lyophilized to afford 0.0755 g (93%) of the title compound as a white solid: FeCl₃ positive (red-purple); mp 111°–113° C.; IR (KBr) 3250 (br), 1750, 1700, 1650, 1625 cm⁻¹; ¹H NMR (300 MHz, D₂O) δ 1.40–1.70 (m, 12H, CH₂), 1.93 (s, 9H, CH₃CO), 3.45–3.55 (m, 6 H, CH₂N), 3.77 (t, 1H, ribose H), 3.88 (d, J=3.0 Hz, 2H, NHCH₂CO), 4.00–4.35 (m, 7H, NCHCH₂ and ribose H), 5.65 (m, 1H, ribose H-1'), 7.66 (d, J=6.3 Hz, 1 H, vinylic H); ¹³C NMR (75 MHz, D₂O) δ 19.26, 19.54, 21.47, 22.19, 22.32, 27.94, 28.10, 28.56, 41.16, 47.02, 47.13, 47.16, 50.80, 50.83, 50.87, 52.74, 53.19, 53.31, 64.08, 69.06, 73.45, 81.05, 89.99, 125.14 (d, J=34.8 Hz, C6), 140.81 (d, J=234.3 Hz, C5), 150.97, 160.47 (d, J=23.7 Hz, C4), 169.16, 170.59, 170.76, 172.97, 173.71, 173.80; MS (positive ion FAB, glycerol/water) m/z 836 (M+1).

Example 12

(N⁶hydroxy-L-lysydroxy-L-lysyl)-N⁵-acetyl-N⁵-hydroxy-L-lysyl)-(L-phenylglycyl)-5-fluorouridine The title compound is prepared by following the procedures and reaction conditions described by Example 10 and by substituting the lysine tripeptide for the ornithine tripeptide.

Example 13

(N⁵-Acetyl-N⁵-hydroxy-L-ornithyl)-N⁵-hyrdroxy-L-ornithyl)-(L-alanyl)-(L-valinyl)-5-fluorouridine The title compound is prepared by first by coupling the hydroxy-protected ornithyl tripeptide, as the active ester formed with N-hydroxysuccinimide, with t-Boc protected alanine followed by coupling the tetrapeptide obtained with 5'-O-(valinyl)-5-fluorouridine and removal of the t-Boc group and the benzyl hydroxy protecting groups.

Example 14

(N⁶-Acetyl-N⁶-hydroxy-L-lysyl)-(N⁶-Acetyl-N⁶-hydroxy-L-lysyl)-(N⁶-acetyl-N⁶-hydroxy-L-lysyl)-(L-phenylalanyl)-L-(Ieucinyl)-5-fluorouridine The title compound is obtained by coupling the hydroxy protected lycine tripeptide as an active ester with an amino protected phenylalanine to obtain the intermediate protected tetrapeptide. The tetrapeptide is then coupled with 5'-O-(leucinyl)-5-fluorouridine and the protecting groups removed to provide the title compound.

We claim:

1. A compound of the formula

R'—NH—CH—C(O)—NH—CH—C(O)—NH—CH—C(O)—NH—
         |              |              |
        (CH₂)p         (CH₂)p         (CH₂)p
         |              |              |
        NHOH           NHOH           NHOH
         |              |              |
        CH₃C(O)        CH₃C(O)        CH₃C(O)

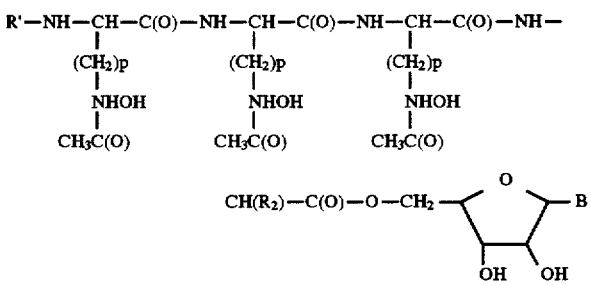

wherein R' is hydrogen or an amino protecting group;
R² is selected from the group consisting of, ethyl, n-propyl, iso-propyl, 2-methylbutyl, and 2-butyl;
p is 3 or 4; and
B is 5-fluorouracil-1-yl or 5-fluorocytosin-1-yl.

2. The compound of claim 1 wherein B is 5-fluoruracil-1-yl.

3. The compound of claim 2 wherein R' is hydrogen and p is 3.

4. The compound of claim 3 said compound being ($N^5$-acetyl-$N^5$-hydroxy-L-ornithyl)-($N^5$-acetyl-$N^5$-hydroxy-L-ornithyl)-($N^5$-acetyl-$N^5$-hydroxy-L-ornithyl)-(L-valinyl)-5-fluorouridine.

5. The compound of claim 2 wherein p is 4.

6. A pharmaceutical composition comprising a compound of claim 1 together with a pharmaceutically acceptable carrier or excipient.

* * * * *